United States Patent
Paul (10) Patent No.: US 6,581,441 B1
(45) Date of Patent: Jun. 24, 2003

(54) CAPILLARY COLUMN CHROMATOGRAPHY PROCESS AND SYSTEM

(75) Inventor: Carlton H. Paul, Groton, MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 0 days.

(21) Appl. No.: 10/061,612

(22) Filed: Feb. 1, 2002

(51) Int. Cl.[7] .................. G01N 30/00; G01N 30/04; B01D 15/08; C12P 19/34
(52) U.S. Cl. .................. 73/61.52; 73/23.42; 210/656; 435/91.1
(58) Field of Search .................. 73/61.52, 61.53, 73/23.42; 210/656; 346/7; 422/100; 435/91.1

(56) References Cited

U.S. PATENT DOCUMENTS

| | | | |
|---|---|---|---|
| 6,210,986 B1 | * | 4/2001 | Arnold et al. .................. 438/42 |
| 6,287,520 B1 | * | 9/2001 | Parce et al. .................. 422/100 |
| 6,379,929 B1 | * | 4/2002 | Burns et al. .................. 435/91.2 |
| 2001/0041357 A1 | * | 11/2001 | Fouillet et al. .................. 435/91.1 |
| 2002/0014106 A1 | * | 2/2002 | Srinivasan et al. .................. 73/23.42 |
| 2002/0176804 A1 | * | 11/2002 | Strand et al. .................. 422/100 |
| 2002/0186263 A1 | * | 12/2002 | O'Connor et al. .................. 346/7 |
| 2002/0187074 A1 | * | 12/2002 | O'Connor et al. .................. 422/82.05 |

* cited by examiner

Primary Examiner—Helen Kwok
Assistant Examiner—J L Politzer
(74) Attorney, Agent, or Firm—Andrew T. Karnakis (57) ABSTRACT

A microfluidic system is provided for separating components of many fluid samples in a parallel fashion through an array of capillary conduits. The system includes capillary conduits for receiving fluid samples, and for effecting separation of substituents of the sample by passing the sample through a corresponding array of capillary separation conduits containing a solid separation medium. The microfluidic circuit is made of three or more substrate layers and preferably includes etched channels in different layers that are dimensioned relative to one another to provide for retaining the solid composition within the capillary separation conduits. The system also includes an array of detector flow cells in fluid communication with the capillary separation conduits, and an array of high pressure connectors for connecting discrete capillary tubes to the fluid passages in the microfluidic circuit for introducing and removing the fluid samples from the system. The connections for the capillary tubes have a small footprint, are readily reversible (allowing ease of maintenance and replacement), and can seal against high pressures.

9 Claims, 6 Drawing Sheets

CAPILLARY COLUMN CHROMATOGRAPHY PROCESS AND SYSTEM

BACKGROUND OF THE INVENTION

This invention relates to an apparatus and method and to system elements for forming capillary columns containing solid separation media within microfluidic circuits for effecting sample analysis, such as chromatography. More particularly, this invention relates to an apparatus and method for forming arrays of capillary channels in a microfluidic circuit, and devices for inserting and retaining solid separation media in the channels, and fluid inlet and fluid outlet connectors for interfacing with the capillary channels, and detection apparatus for monitoring elution gradients or analytes passing through the capillary channels.

Reducing the complexity of biological samples is crucial to the effectiveness of proteomic analysis. Biological samples contain many thousands of components, and a series of sequential separation steps are needed to isolate individual components for analysis. In this procedure, each fraction generated in a previous separation stage undergoes further fractionation. For example, if after the first separation stage 30 fractions are produced, then each of these fractions undergoes a full separation process in the second stage. Each one of the second-stage separations may produce between 30 and 200 fractions (for a total of between 900 and 6000 fractions). The number of sample fractions increases geometrically, but the number of separation processes also increases geometrically. This explosive increase in the amount of separation work is impractical when using current technology. In addition, dividing a single sample into large numbers of fractions can result either in unacceptable dilution of the fractions, or else in the necessity of handling ever-smaller volumes. As the sample volumes become extremely small, the prospect of serious sample losses becomes quite significant.

Conventional chromatography is generally carried out by the passage of a sample mixture through a bed of spherical beads. The beads are tightly packed in a tube or column in a manner to minimize interstitial volume between the beads so as to increase the separation efficiency of the column. The chromatography bed is designed to retard the passage of different components of the mixture to different degrees, resulting in separation of those components as the mixture proceeds through the chromatography bed. An alternative separation medium to chromatography beads is monolithic media which are monolithic blocks taking the form of the containment volume.

Chromatography is highly regarded as a method for separating complex mixtures because several different separation mechanisms are available (such as ion-exchange, reversed-phase, or affinity chromatography). The separation efficiency of well-designed chromatography methods can be quite high, and chromatography can be scaled over a very wide range of volumes. Chromatography would be the method of choice for reducing the complexity of very complex mixtures; however, chromatography lacks sufficient throughput, thus high throughput requires highly parallel operation.

Chromatography at its smallest scale is called capillary chromatography. This is usually conducted in discreet capillaries with internal diameters between 0.01 mm and 0.25 mm filled with packed beds of very small particles or beads. The complementary components required for capillary chromatography, such as column frits, flow cells, and sample injection valves, are also discreet devices to which the capillaries are attached. One of the limitations of capillary chromatography is that the complementary components are generally too large for the scale of the capillary bed, resulting in dispersion of the sample and blending of the separated peaks. Furthermore, the use of discreet components is impractical for arrays of capillary liquid chromatography (LC) systems because of the high cost and the large size of components.

Formation of capillary channels in microfluidic circuits is an attractive alternative to the use of discreet components for making capillary LC systems. As used herein microfluidic circuits refer to, fluid transport and control structures formed within a single substrate made from glass (preferably fused silica), ceramic or plastic materials. Microfluidic circuits enable all of the associated components of a chromatography system to be integrated into one device, appropriately scaled to minimize sample dispersion. Certain critical components required to assemble a chromatography system on a single microfluidic circuit substrate, or an array of systems on a single substrate, are not currently available or, if available, are commercially impractical. For example, the structure for retaining small particles of the chromatography separation medium in larger, conventional chromatography columns is a filter device (sometimes known as a filter frit) that is installed in the fluid path to hold back particles larger than some selected threshold. However, frits are not a viable solution for microfluidic circuit technology. It has been proposed to use devices called Weir filters in photolithographic approaches, but such devices are difficult to manufacture as the depth of the barrier is excessively sensitive to etching depth and this sensitivity has been an impediment to the Weir filter's viability in microfluidic circuits.

An alternative to using small particles as a capillary chromatography medium is to utilize monolithic chromatography beds polymerized directly in place in a capillary. These monolithic media, composed of polymers such as styrene-divinylbenzene copolymers, are porous, uniform blocks taking the form of the containment volume. Examples of the use of such media for capillary chromatography applications are described in U.S. Pat. Nos. 5,130,343; 5,334,310 and 5,453,185. Pumping a mobile phase through the monolithic bed provides unusually fast chromatographic separations because the diffusion distance to the stationary phase is negligible (i.e., tens of nanometers). Just as with discrete separation particles, it is difficult to retain the precursor solution used to form the monolithic bed within the desired separation zone. The fluid precursor to the polymerized bed will tend to flow, pulled by capillary forces, throughout the capillary network rather than being confined to the defined separation zone. This result is undesirable since it is necessary to separate the fluid sample from the solid separation medium so that the fluid sample can be analyzed.

In addition to the problems associated with capillary chromatography set forth above, carrying liquids to a microfluidic circuit or from the microfluidic circuit to a destination off the circuit is difficult because the liquid volumes are extremely small. The transport tubing must be a discrete capillary with a small bore (e.g., 25–150 microns), and the capillary tubing must align and seal with a similarly small hole on the surface of the circuit. The alignment of the capillary to the hole on the circuit is a problem due to the small dimensions, and formation of a reasonably leak-tight seal under the high pressures chromatography systems typically operate is even more difficult. Moreover, at these small dimensions, the surface finish is often coarse compared to the features themselves and this adds to the difficulty in achieving an appropriate seal. A further complication is that the connections should preferably be reversible because large numbers of connections are anticipated and repair or replacement of defective capillaries is desirable. The method of coupling also should have a small footprint to permit high density coupling of connective tubing to the circuit. The coupling technique chosen also must be manufacturable, i.e., it must be possible to automate the process, or at least to assemble such fittings with a minimum of time and rework.

Accordingly, it would be desirable to provide a capillary chromatography process and system contained within a microfluidic circuit as well as system elements that solve the problems set forth above.

SUMMARY OF THE INVENTION

The present invention provides a capillary chromatography process and system contained within a microfluidic circuit that utilizes a solid separation medium confined to a desired capillary containment volume. In one aspect, the solid medium can be either discrete particles or a porous monolithic solid. The solid medium is retained within the desired containment volume by forming capillary paths within a plurality (i.e., 3 or more) of layers that make up the microfluidic circuit. The retainment structures are positioned adjacent to the containment volume of the separation capillary and are formed with channel depths that differ between adjacent layers, thereby creating dimensional restrictions to prevent passage of the discrete solid medium, or of a fluid precursor used to form the monolithic solid medium, but which permit the passage of a fluid sample to be separated by the solid medium.

In one embodiment, the chromatography system includes an array of capillary chromatography columns within the circuit. The use of photolithographic etching processes on fused silica substrates assures that each capillary chromatography element will be a replicate of all other such elements. As a result of using such techniques, a plurality (e.g., 16 or more) of samples can undergo chromatographic analysis in parallel in a highly repeatable fashion.

In still another aspect of the present invention, system connecting elements between discrete capillary transport tubes and the microfluidic circuit are used that allow introduction and removal of fluid streams from the array of capillary chromatographic columns while preventing dispersion of the fluid sample. The connections afford both precision alignment and high pressure alignment necessary to perform chromatography.

DESCRIPTION OF SPECIFIC EMBODIMENTS

In the present invention, retention of small particles within capillary chromatography columns is effected by means of closely controlled restrictions in the dimensions of capillary passages in the microfluidic circuit structure. Specifically, the microfluidic circuit is a three-layer circuit structure composed of individual wafers of fused silica, in which the surfaces of the constituent wafers have been modified by conventional photolithography and etching techniques to create features, including trenches and wells, that define the capillary chromatography structure of the circuit. The retainment structures are formed by creating channels etched to different depths between adjacent wafer layers, thereby creating dimensional restrictions. For example, the middle layer is etched to a depth of between 1 and 3 microns, and the bottom layer is etched more deeply to a depth of between 25 and 80 microns. The etched features in the shallow layer, when bonded with the other layers of the circuit to form internal capillary channels, are too small to allow passage of particles larger than 3 microns in diameter. Holes drilled through the fused silica wafers allow communication between the features in the bottom layer and features in the middle layer. By this means, particles can be packed into a chromatography bed in the bottom layer, where the particles will be retained while fluid passes through capillaries formed in the middle layer.

Also, in accordance with another aspect of the present invention, a liquid precursor used to form a monolithic chromatographic separation composition is positioned within a desired section of a capillary tube by capillary action. One suitable technique involves using liquid precursor compositions for forming a monolithic composition such as are disclosed in U.S. Pat. No. 5,453,185, which is incorporated herein by reference. The same capillary structure that retains solid particles is used; however, flow of the liquid precursor composition is arrested by capillary forces created in the shallow (middle) layer, thereby confining the polymerizing medium to the desired separation region of the fused silica microfluidic circuit.

Another aspect of the present invention is directed to techniques for connecting discrete capillary tubes to the fluid passages in a microfluidic circuit, thereby enabling effective transportation of small fluid streams to and from the fused silica circuit. These connections for the capillary tubes have a small footprint, are readily reversible (allowing ease of maintenance and replacement), and can seal against high pressures.

Figure 1:
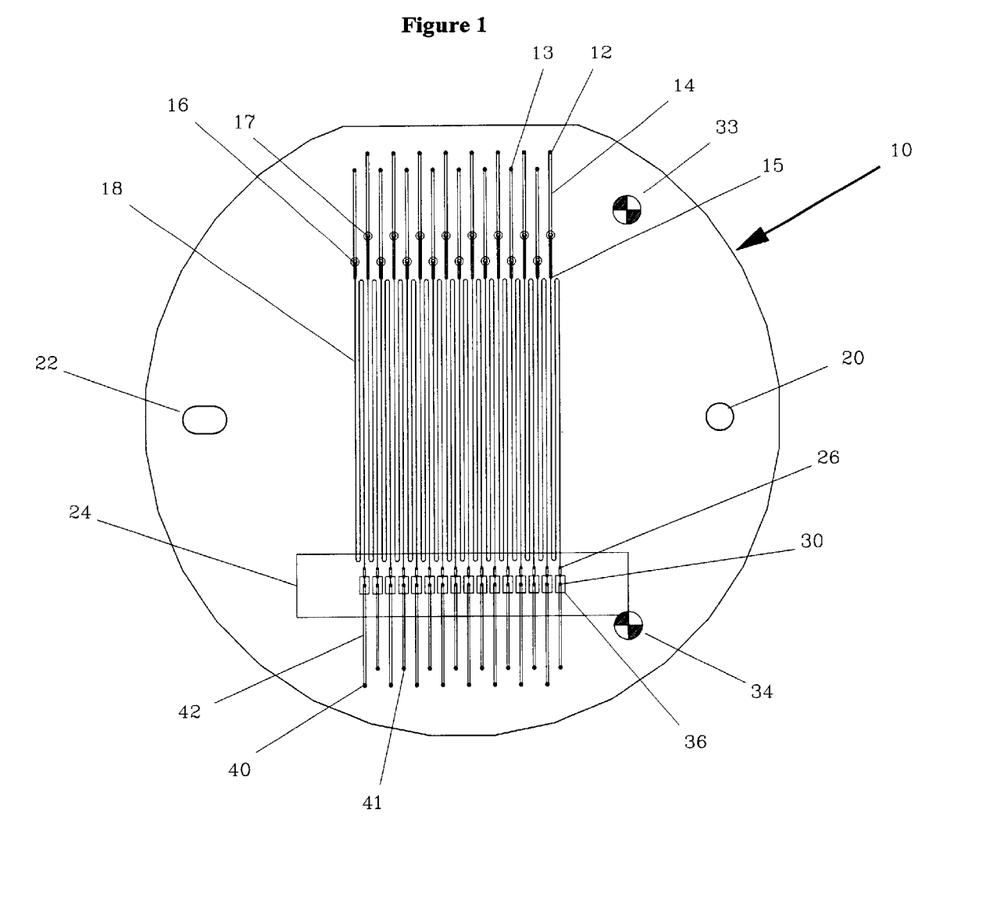
FIG. 1 is a top view of a capillary chromatography microfluidic circuit showing an array of capillary columns in accordance with one embodiment of this invention.

Referring to FIG. 1, a capillary chromatography microfluidic circuit 10 formed of three layers of a glass composition such as fused silica is provided. The circuit 10 includes two staggered rows of capillary inlet ports 12 and 13 and is also provided with two staggered rows of particle inlets 16 and 17. The inlets 16, 17 are utilized to introduce solid particles which effect chromatographic separation in an array of serpentine separation capillary columns 18, that are replicates of one another, arranged in columns across the circuit 10. Sixteen such capillary columns are included in the microfluidic circuit 10. Those skilled in the art will appreciate that fewer or more capillary columns could be included in a microfluidic circuit. Each separation capillary column 18 receives sample to be separated from the inlet ports 12, 13 and each is in fluid communication with respective particle retention microstructures 26, arranged in a row adjacent the outlet end of the capillary column, whose structure and function are more fully described below. To complete the separation process, the particle retention microstructures 26, in turn, are in fluid communication with a row of flow cells 30 which are aligned with a photodiode array (PDA), each individual flow cell being associated with an individual photodiode 36. The flow cells function with a conventional ultraviolet lamp 24 to effect analysis of the fluid samples traversing the flow cells. The flow cells, in turn, are in fluid communication through conduit 42 with two staggered rows of fluid outlets 40 and 41.

The microfluidic circuit 10 is formed from at least three glass layers, preferably wafers of fused silica. Other geometries and materials other than glass may be used as the individual layers, as for example, ceramic or plastic materials. Each layer has etched thereon at fixed locations outside the array of separation columns two optical, circular alignment features 33, 34, which serve as absolute reference positions when forming, such as by drilling, the holes in individual wafers to allow fluid communication between layers. That is to say, rather than measure from the edge of the wafer, whose dimensions may vary from wafer to wafer, the location of holes that are intended to provide fluid communication between two or more layers are indexed to the location of the alignment features 33, 34. The drilling reference point is located at the intersection of two perpendicular diameters of the features 33, 34. Two such features are included to make sure each wafer retains the proper "north-south" orientation. Each layer also is provided with two alignment holes, one hole 20 being circular and the other hole 22 being slotted. The position of holes 20, 22 is located by measuring distances from alignment features 33, 34. A bonding block (not shown) with precision alignment pins that are adapted to pass through holes 20, 22 serve to position the silica wafers when they are bonded together. Because of the small dimensions associated with microfluidic circuit 10, hole 20 should be drilled with tight tolerances with respect to the diameter of the alignment pins (e.g., 0.001"). The slotted hole 22 compensates for slight tolerance mismatches to allow the individual layers to be stacked for bonding. To complete the manufacture of the microfluidic circuit, the individual layers are fusion bonded by application of high temperature to form a single substrate of fused silica. Bonding of the properly aligned silica layers to each other is achieved when they are at a temperature of about 1100° C., and is within the skill in the art.

Figure 2A:
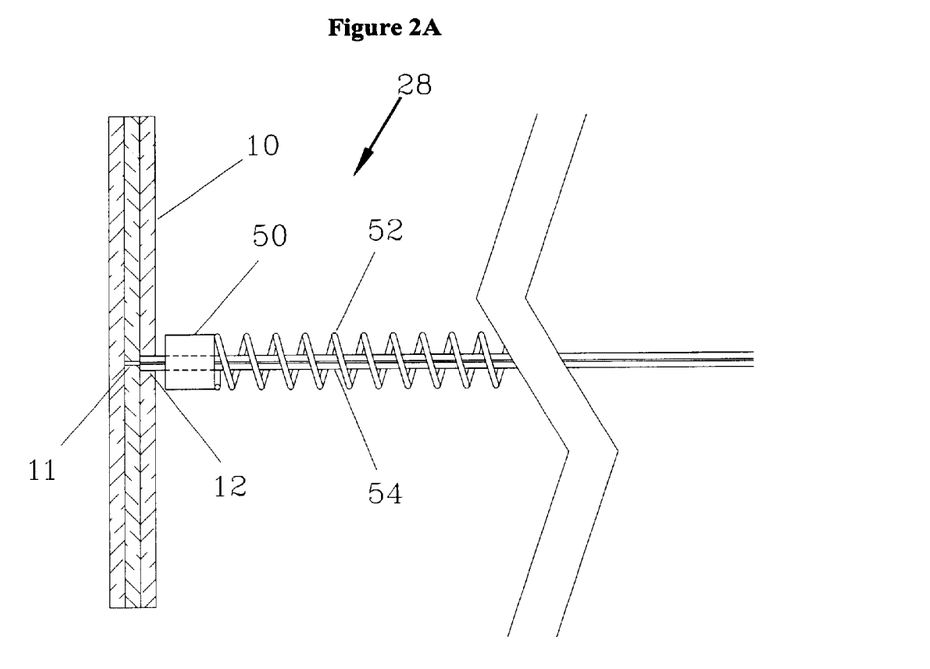
FIG. 2A is a side view of the connector interface between a discrete capillary and the microfluidic circuit shown in FIG. 1.
Figure 2B:
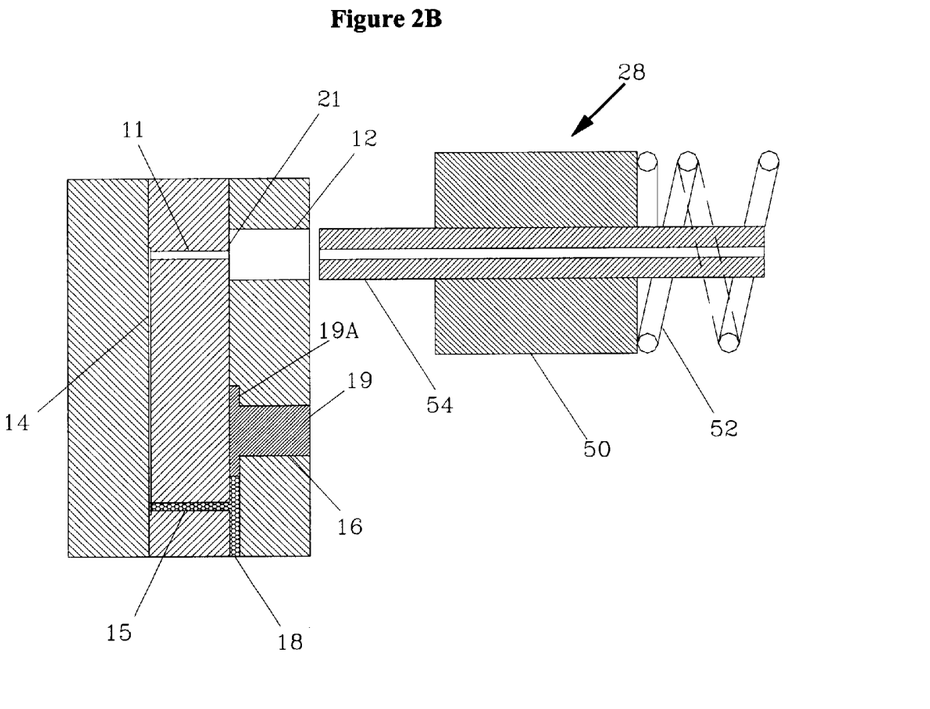
FIG. 2B is an enlarged side view of a fluid inlet element shown in FIG. 2A.

Referring to FIGS. 2A and 2B, an enlarged view of the inlet section of the microfluidic circuit 10 is shown, with attention on a single element of the capillary column chromatography array. The inlet port 12 connects via hole 11 through a shallow channel 14 etched in the second layer of the circuit structure to form an inlet capillary for receiving a fluid sample to be analyzed. A communicating hole 15 passes from the second layer to the separation capillary column 18 formed such as by etching the top surface of the third layer of the structure. However, the separation capillary column 18 in the third layer continues beyond the communicating hole 15 up to a circular cavity 16, at which point a hole in the third layer communicates to the outside surface of the silica circuit. This microstructure is fabricated in this manner for the purpose of packing the capillary 18 with chromatographic media by introducing the media into circular cavity 16, as will be explained in detail below, and is made impermeable to mobile-phase solvent after the media packing operation by the inclusion of plug 19. It is also possible when forming the capillary column 18 to etch the bottom surface of the second layer; however, for ease of microfabrication processing it is preferred to etch the top surface of the third layer.

Referring particularly to FIG. 2B, a cross-section of the high-pressure capillary connector 28 is illustrated. The small hole 11 formed in the second layer, typically with a diameter of less than 200 microns (0.008") and more than 50 microns (0.002"), is used for communicating with the capillary channel 14 in the second layer. Coaxial with this hole is a larger hole formed in the third layer, forming an inlet port 12 for the system. This larger diameter inlet port 12 also serves the function of precisely aligning a discrete capillary tube 54 with the smaller hole 11. The larger inlet port 12 typically has a diameter of about 380 microns (0.015"), which corresponds to the outside diameter of many commercial capillaries. The inlet port 12 thus may be thought of as equivalent to a "counter bore", familiar terminology used on a much larger scale with respect to machined parts, but here formed only after bonding two silica wafers (e.g., the outer and middle wafer) together. The sealing surface 21 of the high pressure connector 28 is formed by the surface of the second layer of the microfluidic circuit, against which a spring 52 through epoxied bead 50 urges the discrete capillary tube 54, and the polished end of capillary tube 54. The surface finish of the sealing face, which is the fused silica wafer, is extremely smooth and the end of the capillary tube is made of compliant material such as PEEK, thereby enabling effective seals against higher pressures. The footprint of the connector 28 is small, typically with a diameter of about 0.06", which is an important advantage in achieving the high densities necessary in creating arrays of numerous separation systems in a single microfluidic circuit. The spring 52 is contained within a counterbore (not shown) of a microfluidic circuit housing 200 (see FIG. 8) and pressing the microfluidic circuit 10 against a lamp housing 202 makes it possible to provide a large number of connections simultaneously and reversibly. This arrangement is therefore highly suitable for assembling large arrays of connectors.

The small hole 11 formed in the second layer communicating between the capillary tube 54 and the shallow channel 14 etched in the top surface of the second layer is aligned to be coaxial with the inlet port 12 that forms the alignment counter bore thereby effecting a highly precise alignment of an external capillary with hole 11 that is necessary when dealing with such small dimensions. Also shown in FIG. 2B is the opening 16 used to pack the separation capillary 18 with separation media. This feature (opening 16) is not intended to be in the fluid transport path of the separation capillary column 18, but rather is meant to form a blind "dog-leg" after the capillary has been packed. This is accomplished (and fluid is prevented from entering this section of the system) by potting in situ the hole 16 and the end of capillary column 18 (after chromatography media has been packed) to create plug 19. The plug is formed of epoxy or another similar, hard and inert substance. The well 19A formed around the access hole 16 provides additional mechanical stability against the possibility that high pressure might blow the potted plug out of the hole.

In one embodiment, the process of filling the chromatography capillary column 18 with a particulate separation medium is achieved by suspending the particulate separation medium in a fluid solvent and pumping this slurry under high pressure into the capillary column 18 through an interface connection to hole 16. This is accomplished by means of a clamp that holds the microfluidic circuit with an O-ring seal around the port and which is in fluid communication with high pressure tubing. For uniform slurry packing, it may be desirable to suspend the slurry in a liquid in which the particles have neutral buoyancy. Of particular note during slurry packing of the structure shown in FIG. 2B, the fluid pathway 15 communicating between the capillary 18 and the fluid inlet port 12 should be plugged by placing a seal over the hole 12. If this is not done, a large part of the pressure drop occurring during slurring packing will occur along this side channel, causing the chromatography media to pack only up to the communicating hole 15. However, prior to completing the slurry packing, the seal over hole 12 should be removed to ensure that the hole 15 is also packed with chromatography medium, as this passage is part of the fluid pathway for the separation process.

Figure 3A:
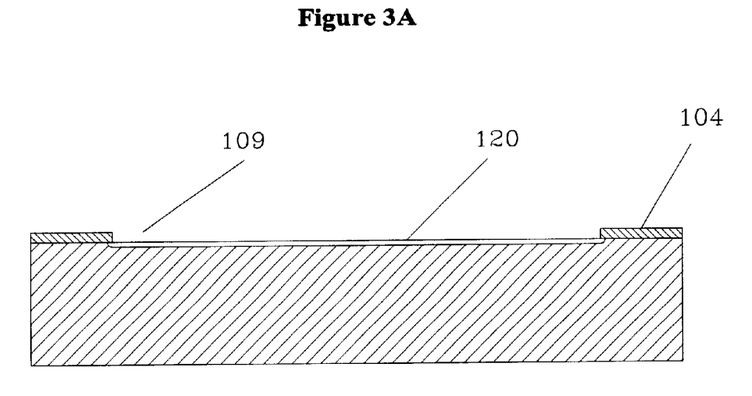
FIGS. 3A and 3B are schematics showing the aspect ratios for etching different depths in layers that are used to form the device shown in FIG. 1.
Figure 3B:
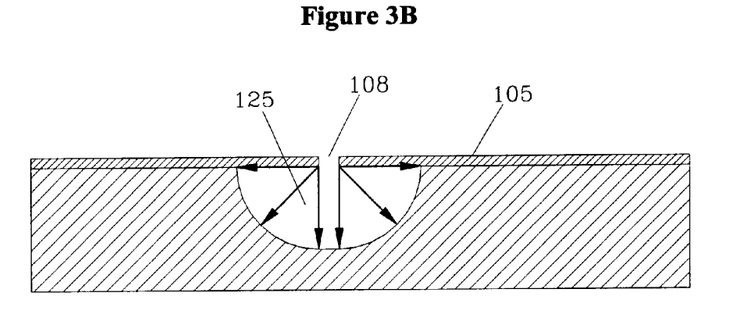

Referring to FIGS. 3A and 3B, a greatly enlarged side view of the features that form the capillary channels 14 (designated by numeral 120 in FIG. 3A) and 18 designated by numeral 125 in FIG. 3B) shows the aspect ratios that are typically required to form a shallow-etch layer and a deep-etch layer. The etching is isotropic (i.e., equal in all directions) in fused silica, and the mask 104 in FIG. 3A is slightly undercut by the etching. The mask feature 109 is wide in order to compensate for the shallow depth of the etching. In contrast, FIG. 3B shows deeper etching with much narrower mask features 108 in the mask 105. However, the deeper etching undercuts the mask 105 much more than it does in FIG. 3A, with the result that the cross section of deep etching is roughly a semicircle.

Referring once again to FIG. 1, each capillary of the array of separation capillaries 18 consists of a three-leg serpentine with a total length of about 10 centimeters. The volumes of the capillaries depend on their etching depth, as can be inferred from the cross sections shown in FIG. 3B. For example, an equivalent circular capillary diameter of 100 microns corresponds to an etching depth of 68 microns, beginning from a mask feature 108 line width of 10 microns. At the top end of the microfluidic circuit 10 adjacent the inlets 16, 17 are the channels used for slurring packing, whereas the actual fluid path for chromatographic separations extends between 15 and 26. The bends in the capillaries appear to have a negligible effect on separation efficiency, and contribute greatly to the device density that can be achieved on a fused silica microfluidic circuit (with favorable consequences on the unit costs of manufacturing chromatography arrays). Those skilled in the art will appreciate that the capillaries need not define tortuous fluid paths; straight capillaries are also within the scope of the present invention.

Figure 4:
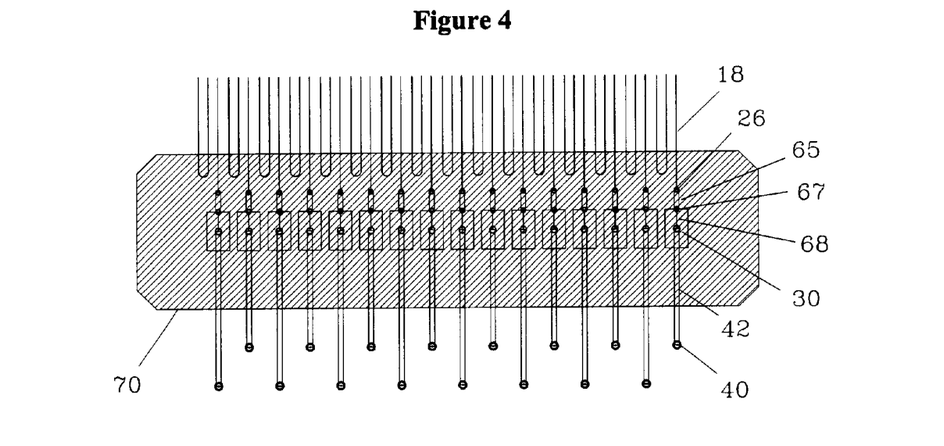
FIG. 4 is a top view of the circuit of FIG. 1 showing details of the outlet end of the separation capillary, including the device for retaining solid chromatography media, the flow cells of the UV detector array, and the port connections to the discrete capillaries.
Figure 5:
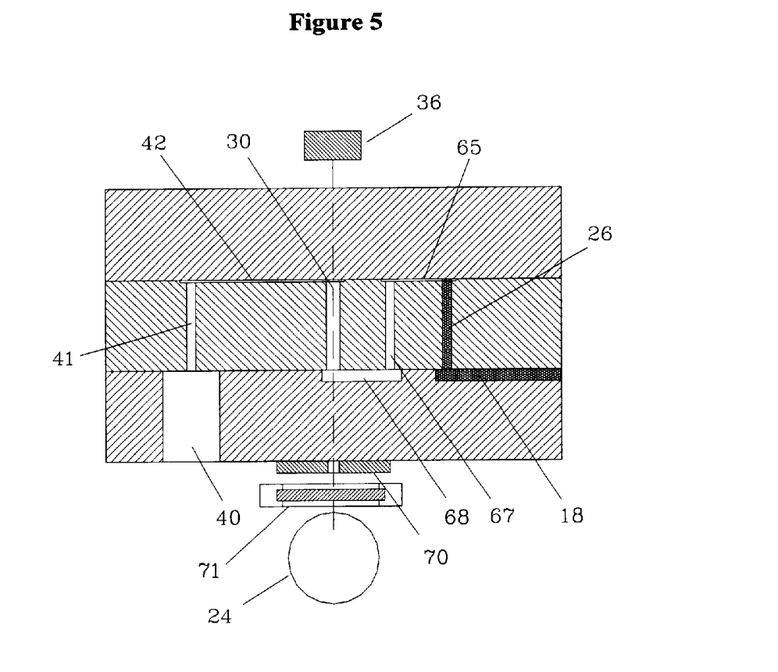
FIG. 5 is an enlarged side view of one system element shown in FIG. 4.

Referring to FIGS. 4 and 5, the outlet end of the separation capillary columns 18, previously shown in FIG. 1, is shown wherein the combination of microstructure 26 and capillary passage 65 is used to retain the particulate chromatography medium in the separation capillary 18 while allowing fluid to flow through the passage 65 formed in the second layer to a communicating hole 67 and then to another passage 68 formed in the third layer, thereafter entering the detector flow cell 30. The flow cell communicates with the outlet port 40 of the circuit by means of a passage 42 in the second layer.

FIG. 5 shows in an enlarged cross-sectional view details of the element shown in FIG. 4. As depicted, the separation medium extends to the top of hole 26 where the dimensions of the etched passage 65 that forms an outlet capillary in the second layer are shallower than the diameters of the particles. As a result, the passage 65 allows passage of fluid while retaining the separation medium in its predetermined containment volume. The fluid path returns to the third (bottom) layer through the hole 67, and passes through the capillary 68 into the flow cell 30. A stainless-steel pinhole mask 70 that covers the flow cell (see FIG. 4) ensures that UV illumination from a lamp is restricted to the flow cell region, and is measured by photodiode 36 on the other side of the microfluidic circuit. The optical path length of the flow cell is 400 microns, and the volume of the flow cell is about 30 nanoliters. The flow cell communicates through a passage 42 in the second layer with an alignment hole/port structure 40, 41 identical to the structure of small hole 11 and capillary inlet port 12 previously shown in FIG. 2B. This flow cell arrangement is similar to the detection scheme described in U.S. Pat. No. 5,757,482 whose disclosure is hereby incorporated by reference.

The pinhole mask 70 contains a plurality of pinholes, in this case sixteen holes, insuring that the UV lamp illuminates only the flow cells. Thus stray light that could saturate the optical detector is eliminated or greatly minimized. A mercury plasma lamp 24 with a major emission line at 253 nm or a zinc plasma lamp with a major emission line of 214 nm can be used. A bandpass filter 71 centered at 254 nm (for Hg) or 214 nm (for Zn) removes illumination that is not absorbed by the selected analytes. The mask 70 is retained in place by an adhesive such as epoxy bonded directly to the microfluidic circuit. Since the alignment tolerances are quite demanding, temporary tabs (not shown) are used for aligning the mask with the row of flow cells under a microscope, and are snapped off after the adhesive has set.

Figure 6:
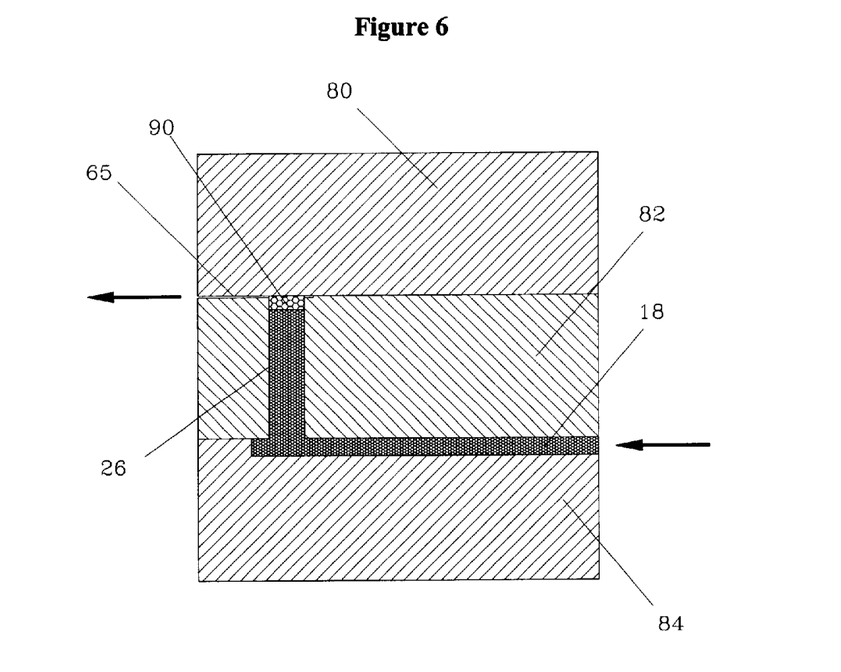
FIG. 6 is an enlarged side view of the device for retaining solid chromatography particles in the separation capillary.

FIG. 6 is an enlarged view of the structure for retaining small diameter chromatography media within the capillary column shown in FIG. 5. A capillary flow path is shown which extends through two silica wafer layers of the microfluidic circuit, namely the bottom layer 84 and the middle layer 82. Liquid from a separation capillary 18 enters a hole 26 communicating with a much shallower etched capillary 65. The hole 26 has a diameter of between 50 and 150 microns, which is large enough to permit passage of small particles from the separation capillaries 18. Fluid from hole 26 passes through capillary 65 having an etched depth between about 1 micron and 3 microns, which is small enough to retain typical 5 micron diameter particles of the separation medium therein so that particles are prevented from entering the flow cells. By configuring the capillaries 18, 65 and the communicating hole 26 in this manner fluid sample can flow through the flow cells while avoiding particle passage through the flow cells.

FIG. 6 illustrates how it is possible to retain particles much smaller than even the etching dimensions of the shallow layer by packing a short section 90 of the communicating hole with particles that are retained, followed by a packed bed of much smaller particles. It would also be possible to sinter the larger particles in place by means of high temperature. However, in this instance, since no separation medium would survive the high temperatures of bonding or sintering, the smaller particles must be added after all high-temperature processing steps are complete.

Figure 7A:
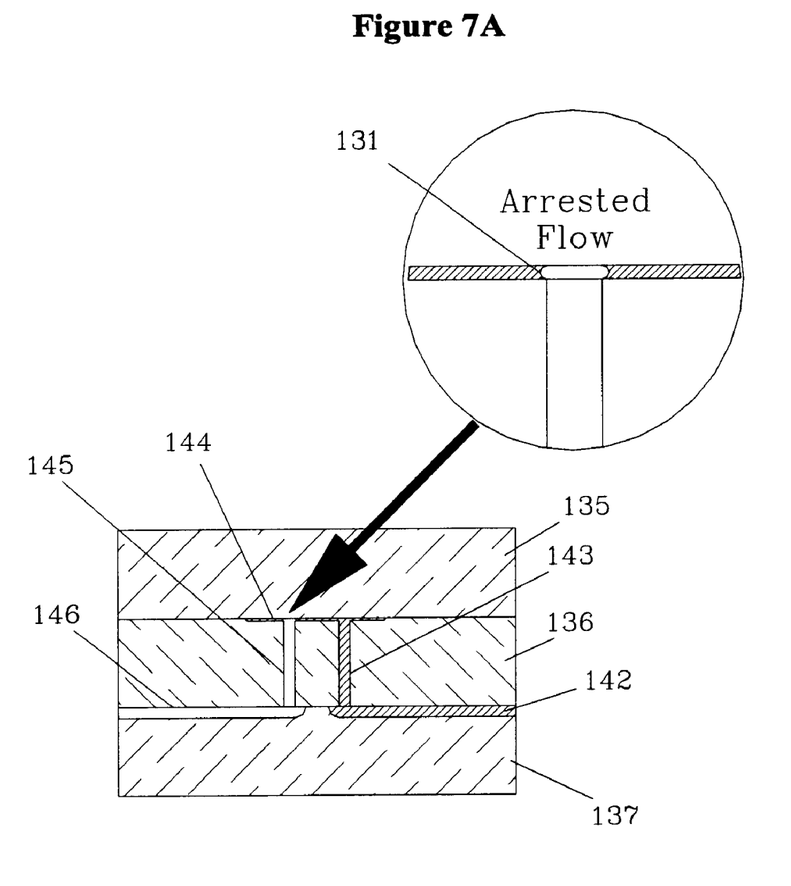
FIG. 7A is an enlarged side view of the same device shown in FIG. 6, used instead to contain a polymerizing solution to create a monolith within the separation capillary.
Figure 7B:
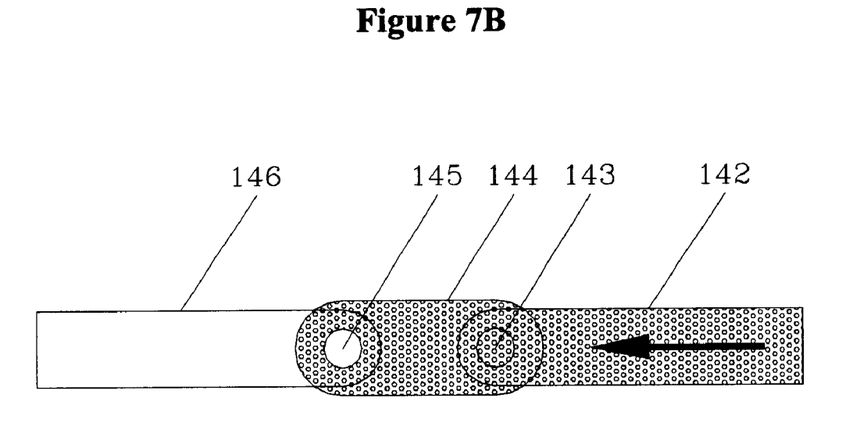
FIG. 7B is a top view of the device shown in FIG. 7A.

FIGS. 7A and 7B show another embodiment for adding a monolithic separation media to a capillary column. Here a flow path is shown which is designed to isolate a polymerizing fluid within a capillary as precursor to formation of a monolithic separation medium. The fluid flow path is formed from three layers 135, 136 and 137 of the fused silica microfluidic circuit 10 having the fluid paths etched and drilled therein. The fluid path comprises separation-capillary 142, drilled hole 143 and a shallow capillary 144.

Path 144 has a depth less than about 5 microns so that a fluid meniscus 131 in this region will have a very small radius of curvature. The very small dimensions will produce strong capillary forces that pull the fluid into the capillary 144, but prevent fluid from continuing down the hole 145. This flow path is designed so that a liquid precursor to a monolithic chromatography bed will be contained within the desired separation volume without spreading through the flow cell and other parts of the capillary network. The liquid precursor comprises a polymerizable monomer, a polymerization initiator and a porogen as taught in the aforementioned U.S. Pat. No. 5,453,185. The liquid then can be polymerized in-situ within the capillary to form a porous polymeric column. The volume comprising the drilled hole 145 and flow path 146 is free of the liquid precursor to the monolithic chromatography bed.

Figure 8:
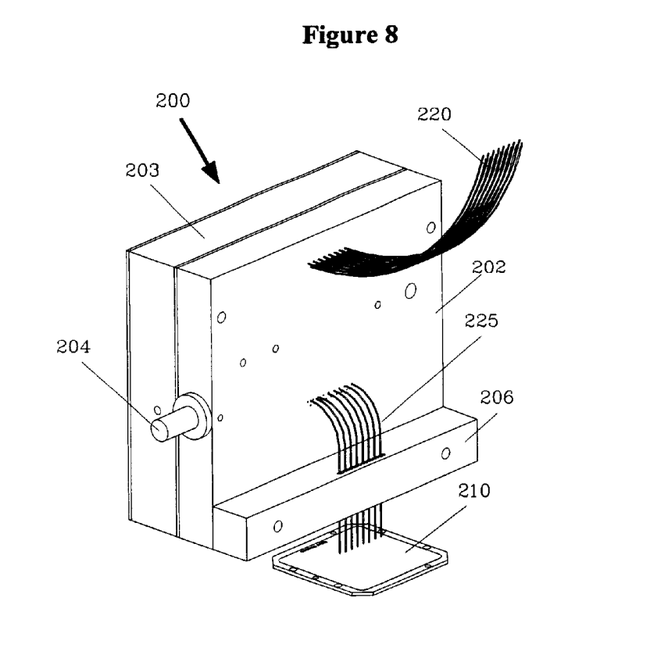
FIG. 8 is an isometric view of the system that houses the chromatography microfluidic circuit array, including the inlet and outlet capillaries, the UV lamp, the photodiode array detector, and a MALDI plate on which fractions are collected.

Referring to FIG. 8, the housing 200 that contains the microfluidic circuit 10 consists of a lamp block 202, a Mercury (Hg) lamp 204, and a photodiode array block 203 containing both the PDA and its associated electronics. A bundle of inlet capillary tubes 220 for feeding samples and solvents into the array of chromatography capillaries and a corresponding bundle of outlet capillary tubes 225 transporting the separated components from the chromatography capillaries to a MALDI plate 210, where fractions are deposited, interface with the housing. A guide block 206 aligns the capillary tubes 225 in a tight row for deposition on the MALDI plate 210.

Figure 9:
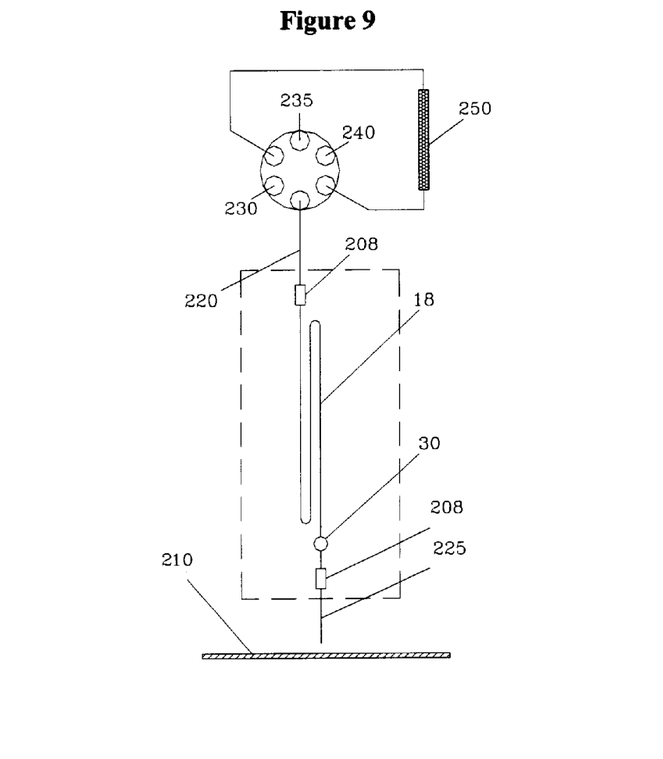
FIG. 9 is a schematic of one separation element of the chromatography microfluidic circuit array, depicting the introduction of a fluid sample, its separation and detection, and the removal of sample from the circuit. Elements formed within or on the microfluidic circuit are shown within the dashed line, and those elements external to the microfluidic circuit are outside the dashed line.

Referring to FIG. 9, a schematic diagram of a single separation element, packed with appropriate chromatography media as previously described, is shown wherein those components in or associated with the microfluidic circuit 10 are contained within a dashed line. A source of mobile-phase solvent at high pressure enters a six-way valve at port 230, wherein one position of the valve diverts the solvent directly to the capillary chromatography column 18 through a section of a discreet capillary tube 220. In this same valve position, a sample can be introduced at port 235, wherein it is transported through a trapping column 250 that binds the mixture of analytes in the sample. The outlet of the trapping column 250 emerges from a waste port 240. In the other valve position, the high pressure mobile-phase solvent is diverted through the trapping column 250 and enters the chromatography capillary column 18, thereby displacing the mixture of analytes bound to the trapping column 250 and beginning their separation on the capillary chromatography column. The discreet capillary tube 220 connecting the valve to the chromatography capillary 18 includes a high-pressure connector 208. At the conclusion of the separation, the fluid passes through a UV detector flow cell 30, allowing monitoring of either the gradient used in the separation, or of the analytes emerging from the chromatography capillary column 18. The fluid then passes through another high pressure connector 208 to a discreet capillary 225, wherein it is transported and deposited on a MALDI plate 210. By this means, the separated fractions obtained from the chromatographic separation are made available for further analysis, as, for example, by time-of-flight mass spectrometry.

I claim:

1. A microfluidic circuit for separating components of a fluid sample comprising:
   a first capillary of first etched depth formed in a first region of the circuit adapted to receive the fluid sample;
   a second capillary of second etched depth larger than that of the first capillary formed in a second region of the circuit in fluid communication with the first capillary;
   a third capillary of third etched depth smaller than that of the second capillary formed in a third region of the circuit in fluid communication with the second capillary;
   a solid composition contained within the second capillary capable of effecting separation of the components of the sample;
   wherein the solid composition comprises solid particles and the etched depths of the first and third capillary are smaller than the size of the solid particles to retain the particles within a desired containment volume of the second capillary and being sufficiently large to permit passage of the fluid sample therethrough.

2. The circuit of claim 1 including a flow cell in fluid communication with the second capillary and a detector in association with the flow cell to analyze the components of the sample.

3. The circuit of claim 2 wherein the detector is an optical detector.

4. The circuit of claim 1 comprising at least three distinct glass substrates bonded together and wherein at least two adjacent substrates have features etched therein to form the first, second and third capillary after the substrates are bonded.

5. The circuit of claim 4 wherein the glass substrate is fused silica.

6. The circuit of claim 5 wherein the substrates are fusion bonded.

7. The circuit of claim 4 wherein a first surface of one of the substrates is etched to a first width and depth and a second surface of an adjacent substrate is etched to a second, different width and depth, the second surface being that surface which does not face the first surface when the substrates are bonded; and
   wherein holes extend through the adjacent substrate to provide fluid communication between the first, second and third capillary.

8. A process for separating and analyzing components of a fluid sample using the microfluidic circuit of claim 1 comprising:
   providing a multi-layer microfluidic circuit formed of at least three glass layers;
   introducing the fluid sample into said first capillary formed in a first layer of the microfluidic circuit;
   passing the sample from said first capillary to said second capillary formed in a second adjacent layer of the microfluidic circuit;
   passing the sample from said second capillary to said third capillary and then to a flow cell in fluid communication with said second and said third capillary; and
   providing a detector in association with said flow cell for analyzing the components of the separated fluid sample.

9. The process of claim 8 wherein said detector is an optical detector.

* * * * *